United States Patent [19]

Shah

[11] 4,322,551

[45] Mar. 30, 1982

[54] PROCESS FOR PREPARING AROMATIC AMIDE ANTIOXIDANTS

[75] Inventor: Niranjan V. Shah, Stow, Ohio

[73] Assignee: The Goodyear Tire & Rubber Company, Akron, Ohio

[21] Appl. No.: 878,199

[22] Filed: Feb. 16, 1978

[51] Int. Cl.$^3$ ............................................. C07C 102/06
[52] U.S. Cl. ................................. 564/137; 260/404.5; 564/134; 564/135
[58] Field of Search ................ 252/431 R; 260/558 P, 260/562 R, 562 P, 557 R, 562 N, 404.5; 564/134, 135, 137

[56] References Cited

U.S. PATENT DOCUMENTS

| | | | |
|---|---|---|---|
| 2,265,949 | 12/1941 | Loder et al. | 252/431 R X |
| 3,462,486 | 8/1969 | De Feo | 260/558 P X |
| 3,538,159 | 11/1970 | Duffy | 260/561 R |
| 3,907,893 | 9/1975 | Parker | 260/562 R |
| 4,105,693 | 8/1978 | Chiyomaru et al. | 260/558 P |

OTHER PUBLICATIONS

Streitwieser, Jr. et al., "Acidity of Hydrocarbons XXXIX" in JCS, vol. 94, No. 14, 7/12/1972 pp. 4888-4891.

*Primary Examiner*—Thomas A. Waltz
*Attorney, Agent, or Firm*—J. Y. Clowney

[57] ABSTRACT

A process for the preparation of aromatic amide antioxidants from a simple aliphatic or aromatic ester and primary amine in the presence of a metal alkoxide and an alcohol. Unsaturated products produced using this process are sufficiently pure to use as comonomers in the preparation of elastomers.

8 Claims, No Drawings

PROCESS FOR PREPARING AROMATIC AMIDE ANTIOXIDANTS

This invention relates to an improved process for preparing antioxidant compositions. More particularly the invention relates to a process for preparing aromatic amides which give polymer compositions containing these aromatic amides a high degree of resistance to the deleterious effects of oxidative aging over a prolonged period of time.

U.S. Pat. No. 3,907,893 reveals the preparation of amide antioxidants by reacting simple aliphatic or aromatic esters with aromatic amines in an organic solvent in the presence of a base to form a metallic salt and hydrolyzing the salt with a dilute acid to form the amide. Both reaction rate and yields are less than desired.

It is another object of the present invention to provide an improved process of manufacturing amide antioxidants. Further objects will become apparent to those skilled in this art as the description proceeds.

In accordance with the present invention amides are synthesized by reacting simple aliphatic or aromatic esters, both saturated and unsaturated, having the general formula (A)

(A)

with aromatic amines having the general formula (B)

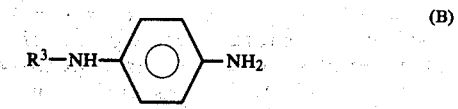

(B)

in the presence of (C) a base selected from the group consisting of alkali metal alkoxides and alkali metal amides and (D) an alcohol. The reaction produces a metallic salt which is removed from the solution, washed with an organic solvent and hydrolyzed, e.g., with dilute acid to form antioxidant amides of the general formula (E)

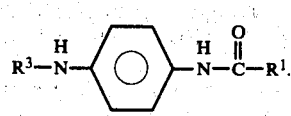

The metallic salt has the following structure:

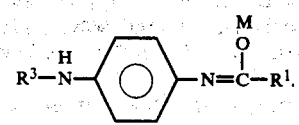

$R^1$ is a radical selected from the group consisting of alkyl radicals having from 1 to 20 carbon atoms, alkenyl radicals having from 2 to 10 carbon atoms, aryl radicals having from 6 to 12 carbon atoms and cycloalkyl radicals having from 5 to 12 carbon atoms. $R^2$ is a radical selected from the group consisting of alkyl radicals having from 1 to 10 carbon atoms, and $R^3$ is a radical selected from the group consisting of alkyl radicals having from 1 to 20 carbon atoms, cycloalkyl radicals having from 5 to 12 carbon atoms, aryl radicals having from 6 to 12 carbon atoms and aralkyl radicals having from 7 to 13 carbon atoms. M is an alkali metal.

Representative examples of radicals $R^1$, $R^2$ and $R^3$ useful in the practice of this invention are alkyl radicals such as methyl, ethyl, butyl, pentyl, octyl, decyl, tetradecyl and eicodecyl; aryl radicals such as phenyl naphthyl and pentyl phenyl; cycloalkyls such as cyclopentyl, cyclohexyl, dicyclohexyl cycloheptyl and cyclododecyl; aralkyl radicals such as benzyl, methyl benzyl, heptyl phenyl and ethyl phenyl and alkenyl radicals such as ethenyl, propenyl, butenyl, pentenyl, hexenyl, octenyl, nonenyl and decenyl.

The process of the present invention is carried out in an organic solvent other than alcohol. Solvent as used herein is any inert organic liquid in which the ester is soluble. Preferably the amine will also be soluble in the solvent. Representative examples of solvents useful in the process of this invention are benzene, toluene and xylene. Xylene is a preferred solvent.

Representative examples of the compounds which can be used and are produced in the practice of this invention are listed in column 2, lines 52–68 and column 3, lines 1–27 of U.S. Pat. No. 3,907,893. It should be noted that the structural formula for the amide antioxidants is designated as (E) herein, but is designated as (D) in the aforementioned patent.

Alcohols which can be used in the practice of the present invention conform to the following structural formula $R^4OH$ wherein $R^4$ is an alkyl group of 1 to 6 carbon atoms. The alcohol selected for a particular reaction must be capable of dissolving the metal alkoxide and must be used in an amount sufficient to do so. The alcohol also preferably possesses a boiling point which is lower than that of the solvent and the ester. Alcohols which can be used include but are not limited to methanol, ethanol, isopropanol and butanol. Preferably $R^2$, $R^4$ and $R^5$ are identical. Although excess amounts of alcohol can be used it is only necessary that enough alcohol be used to dissolve the alkoxide.

The alkali metal alkoxides preferably have the following structure $R^5OM$ wherein $R^5$ is an alkyl radical having 1 to 6 carbon atoms such as methyl or ethyl and wherein M is an alkali metal such as sodium, potassium or lithium.

Alkali metal amides can also be used as the base in this reaction since the alcohol reacts with the amides and forms corresponding alkoxide and ammonia gas. The alkali metal amides preferably have the following structure $MNH_2$ wherein M is an alkali metal such as sodium, potassium or lithium. Consideration should be given to this fact in determining the amount of alcohol to be used.

The reaction described herein results in formation of the desired product which is the alkali amine salt and a by-product which is the alcohol. Since this is a reversible stoichiometric reaction the removal of the by-product alcohol from the reaction system should result in a favorable equilibrium yield of the salt. The addition of the alcohol in the reaction system, therefore, should result in a lower yield since it would theoretically shift the equilibrium to the left.

To the contrary, it has been discovered that the addition of alcohol to the reaction system provides an increased yield of the salt. This is apparently due to the homogeneity of the reaction system brought about by the solubility of the alkoxide and the reaction product, the alkali amine salt (as it is being formed) in the alcohol. The homogeneity of the reaction mass increases the reaction rate considerably and if the alcohol is removed from the system at a controlled rate, a higher equilibrium yield of the salt is realized.

The removal of the alcohol is absolutely necessary since it would not only affect the equilibrium by its concentration effect but being a low boiler it will also prevent the system from achieving higher reaction temperature. The amidation reactions described herein are all endothermic reactions, higher reaction temperature therefore favoring higher equilibrium yield. Higher temperature can also be achieved by reacting under pressure until desired temperature is reached and then removing the alcohol through special control devices without disturbing the whole reaction system.

Ideally alcohol is added initially to the reaction mixture and then removed continuously to raise the reaction temperature. The alcohol added should be sufficient to keep the alkoxide dissolved. As the reaction proceeds the alkoxide is converted to the alcohol. The level of alcohol is thus maintained such that at least part way through the reaction the salt product also stays dissolved, forming a homogenous reaction system. In other words, it is desirable to keep the alcohol concentration as low as possible while still maintaining solubility.

As the reaction proceeds it reaches a point where the system is no longer homogenous, i.e., the amount of alcohol present is not enough to keep the reaction product dissolved. It is believed at that point most of the alkoxide has reacted and that optimum conversion to the salt has taken place. In Example 1 which appears subsequently herein solids were first observed when the reaction temperature reached 115° C. The reaction temperature rose rapidly from there on and the solids were observed precipitating out of the solution at a rapid rate. The reaction was assumed to have reached a completion when the reaction temperature reached the boiling point of the solvent, i.e., 138° C., and when the column outlet temperature started to rise beyond the boiling point of the alcohol/ester azeotrope.

The process comprises combining approximately equivalent molar amounts of the primary aromatic amine, ester and metal alkoxide together with a suitable organic solvent and alcohol. Although equivalent molar amounts are not an absolute necessity such amounts are the most practical from an economic standpoint. Preferably a solution of alkoxide in alcohol is prepared followed by the addition of the organic solvent, amine and ester, preferably in that order. If desired, the ester can be added slowly during the reaction.

A preferred method involves heating the mixture of amine, ester, alkoxide, alcohol and organic solvent until the boiling point of the solvent is reached. During the heating period the metallic base abstracts a hydrogen from the amine, replacing it with metal and forming an alcohol, preferably the same one used for dissolving the alkoxide, and an alkali amine salt. The alcohol and/or alcohol/ester azeotrope and/or alcohol/solvent azeotrope distillate is removed continuously, preferably through a packed column. The column outlet temperature preferably is controlled in such a way that only an azeotropic amount of ester and/or solvent is removed with the alcohol. The distillate is cooled. The intermediate metal salt formed is removed from solution and washed with an organic solvent such as hexane, toluene or xylene, until the washed solution is clear. The salt is dried and hydrolyzed with dilute acid to form a solid product. The solid product is then removed from solution and air dried at room temperature. This ester process produces no troublesome by-products.

The primary amines and base can be mixed in any molar ratios desired. The most preferred molar ratio is 1:1 amine:base, although molar ratios of from 1:10 to 10:1 amine:base can be used. The primary amine:base mixture is added to the ester in a molar ratio of from 10:1 to 1:10 amine:ester. The reaction between the amine and the ester is essentially a 1:1 molar reaction such that an excess of one reactant over the other has no effect on the reaction.

The amide compounds described herein are useful as antioxidants in elastomers as described in U.S Pat. No. 3,907,893.

The following examples illustrate the practice of the present invention. Unless otherwise indicated all parts and percentages are by weight.

EXAMPLE 1

A one liter flask equipped with an agitator was charged with 90 grams of methanol and 30 grams (0.55 mol) of sodium methoxide while under a slow $N_2$ purge. The mixture was stirred until solution was achieved. 450 milliliters of xylene followed by 92 grams (0.5 mol) of p-aminodiphenylamine and 70.8 (0.71 mol) of methylmethacrylate were added to the flask while agitating. The homogeneous solution was then slowly heated and methanol was removed through a packed column. Methanol forms an azeotrope with methylmethacrylate and thus the distillate contained some methylmethacrylate as well as some xylene. Approximately 120 grams of distillate was removed over a period of two hours, during which the column outlet temperature stayed at 62°–63° C. while the flask temperature rose from 90° C. to 138° C. The column outlet temperature then started climbing, indicating the absence of methanol. The flask was then cooled to 70° C. and the sodium salt was filtered through a Buchner funnel. The salt was first washed with xylene to remove the residual amine and then with hexane. The salt was allowed to air dry and then restirred in one liter of cold water. It was then hydrolyzed with 10 percent sulfuric acid to pH of about 6. The product was filtered and air dried yielding 101 grams of N-(4-anilinophenyl) methacrylamide having a melting point of 102°–103° C. The yield was 80.15 percent.

When commercially available 25 percent solution of sodium methoxide in methanol was used in place of powder and methanol no appreciable difference in the reaction or yield was observed.

The example illustrates that higher rates of reaction and higher yields are obtained when using alcohol as opposed to the process of U.S. Pat. No. 3,907,893 where no alcohol is used.

Some compounds yield intermediate salts which are liquids or semi-solids. Such salts are not susceptible to filtration but can be extracted or washed by decantation of the solvent. The present process is applicable, with variation of separation techniques, to various amides.

Where the intermediate salts are solids the present process has the additional benefit over the process of U.S. Pat. No. 3,907,893 in that the intermediate salt is incapable of coating the alkoxide as it can in the process of the subject patent since the alkoxide in the present process is in solution.

While certain representative embodiments and details have been shown for the purpose of illustrating the invention it will be apparent to those skilled in this art that various changes and modifications may be made herein without departing from the spirit or the scope of the invention.

What I claim is:

1. An improved process for the synthesis of an antioxidant amide comprising reacting a simple aliphatic or aromatic ester, either saturated or unsaturated having the general formula (A)

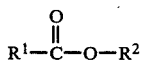
(A)

with an aromatic amine having the general formula (B)

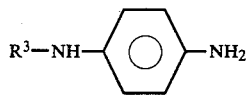
(B)

in an organic solvent and in the presence of (C) a base selected from the group consisting of alkali metal amides and alkali metal alkoxides, to yield an intermediate metallic salt, and hydrolyzing the salt to form an antioxidant amide of the general formula (E)

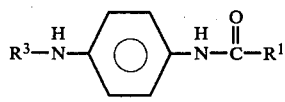
(E)

wherein $R^1$ is selected from the group consisting of alkyl radicals having from 1 to 20 carbon atoms, aryl radicals having from 6 to 12 carbon atoms, cycloalkyl radicals having from 5 to 12 carbon atoms, alkenyl radicals having from 2 to 10 carbon atoms, $R^2$ is selected from the group consisting of alkyl radicals having from 1 to 10 carbon atoms, and alkenyl radicals having from 2 to 10 carbon atoms and wherein $R^3$ is selected from the group consisting of alkyl radicals having from 1 to 20 carbon atoms, cycloalkyl radicals having from 5 to 12 carbon atoms, aryl radicals having from 6 to 12 carbon atoms and aralkyl radicals having from 7 to 13 carbon atoms,—wherein—the improvement—comprises: (1) adding—an alcohol (D)—to the reaction before the beginning of the reaction, said alcohol (a) being a solvent for the metal alkoxide (C), (b) being added in sufficient quantity to dissolve the metal alkoxide, and (c) having the formula $R^4OH$, wherein $R^4$ is an alkyl group of 1–6 carbon atoms, and (2) continuously removing the alcohol during the reaction to raise the reaction temperature.

2. A process as described in claim 1 above wherein the ester is selected from the group consisting of methyl methacrylate, ethyl laurate, methyl isobutyrate, methyl benzoate, methyl phenyl acetate, ethyl cinnamate, ethyl crotonate and ethyl acetate.

3. A process as described in claim 2 wherein the primary aromatic amine is selected from the group consisting of p-aminodiphenylamine; N-isopropyl paraphenylene diamine; 2,6-di-t-butyl-4-aminophenol; N-hexyl paraphenylenediamine; 2,6-di-t-hexyl-4-aminophenol and N-cyclohexyl paraphenylene diamine.

4. A process as described in claim 3 wherein the reaction takes place in the presence of a metal alkoxide selected from the group consisting of sodium methoxide, potassium tert. butoxide, lithium methoxide, sodium tert. butoxide and sodium ethoxide—and the molar ratio of amine to metal alkoxide is about 1:1.

5. A process as described in claim 4 wherein the reaction occurs in the presence of an alcohol selected from the group consisting of methanol, ethanol, isopropenyl and butanol.

6. A process as described in claim 5 wherein the ester is methyl methacrylate, the amine is p-aminodiphenylamine, the alkoxide is sodium methoxide and the alcohol is methanol.

7. A process as described in claim 6 wherein the organic solvent is selected from the group consisting of xylene, benzene and toluene.

8. A process according to claim 1 wherein the intermediate metallic salt is a solid.

* * * * *